US007927562B2

(12) United States Patent
Wan et al.

(10) Patent No.: US 7,927,562 B2
(45) Date of Patent: Apr. 19, 2011

(54) COLLECTION AND ASSAY DEVICE FOR BIOLOGICAL FLUID

(75) Inventors: John Wan, San Marino, CA (US); Zhijing Wan, Beijing (CN); Chunhua Yuan, Zhejiang (CN); Siyu Lei, Beijing (CN)

(73) Assignee: W.H.P.M. Inc., El Monte, CA (US)

( * ) Notice: Subject to any disclaimer, the term of this patent is extended or adjusted under 35 U.S.C. 154(b) by 405 days.

(21) Appl. No.: 11/956,176

(22) Filed: Dec. 13, 2007

(65) Prior Publication Data

US 2009/0155124 A1 Jun. 18, 2009

(51) Int. Cl.

| | |
|---|---|
| ***G01N 21/75*** | (2006.01) |
| ***G01N 31/22*** | (2006.01) |
| ***G01N 33/52*** | (2006.01) |
| ***G01N 15/06*** | (2006.01) |
| ***G01N 33/00*** | (2006.01) |
| ***G01N 33/48*** | (2006.01) |
| ***G01N 1/10*** | (2006.01) |
| ***B01L 3/00*** | (2006.01) |

(52) U.S. Cl. ........ 422/406; 422/401; 422/405; 422/430; 422/68.1; 422/547; 422/549; 436/180

(58) Field of Classification Search ........................ None
See application file for complete search history.

(56) References Cited

U.S. PATENT DOCUMENTS

| | | | | |
|---|---|---|---|---|
| 4,978,504 | A | 12/1990 | Nason | |
| 5,268,148 | A | 12/1993 | Seymour | |
| 6,248,598 | B1 | 6/2001 | Bogema | |
| 6,821,788 | B2 | 11/2004 | Cesarczyk | |
| 7,029,627 | B2 | 4/2006 | Alley | |
| 7,192,555 | B2 | 3/2007 | Mink et al. | |
| 7,507,373 | B2 * | 3/2009 | Vallejo et al. | 422/56 |
| 2004/0019301 | A1 | 1/2004 | Wong et al. | |
| 2005/0180882 | A1 * | 8/2005 | Tung et al. | 422/61 |
| 2006/0127274 | A1 * | 6/2006 | Vallejo et al. | 422/56 |
| 2006/0210448 | A1 * | 9/2006 | Wang et al. | 422/102 |
| 2007/0275475 | A1 * | 11/2007 | Liang | 422/68.1 |

FOREIGN PATENT DOCUMENTS

| | | |
|---|---|---|
| WO | WO 95-02996 A1 | 2/1995 |
| WO | WO 03-060479 A2 | 7/2003 |

OTHER PUBLICATIONS

International Search Report dated Nov. 9, 2009 issued in PCT/US2009/036003.

* cited by examiner

*Primary Examiner* — Jill Warden
*Assistant Examiner* — Charles Hammond
(74) *Attorney, Agent, or Firm* — Scully, Scott, Murphy & Presser, P.C.

(57) ABSTRACT

A device for collecting and analyzing a biological fluid is provided. The device contains a sample collecting section having at least one collection pad for collecting a sample of the biological fluid, a sample accommodating section operatively engageable with the sample collecting section for extracting and accommodating the sampled collected by the sample collecting section, a sample analyzing section, disposed within the sample accommodating section and having a sample analyzing means in fluid communication with the sample extracted and accommodated within the sample accommodating section.

9 Claims, 6 Drawing Sheets

COLLECTION AND ASSAY DEVICE FOR BIOLOGICAL FLUID

BACKGROUND OF THE INVENTION

1. Field of the Invention

The present invention generally relates to a diagnostic device. More particularly, this invention relates to a device for collecting and analyzing a biological fluid.

2. Related Art

Analytical devices for collecting samples and determining the presence or absence and/or quantifying the amount of various analytes in the samples are known in the market. Assays are usually available for abused drugs, pregnancy and fertility testing, and infectious diseases. Most of these existing analytical devices are typically designed and used to analyze urine samples for testing DOA (Drugs Of Abuse) chemicals. Urine has the traditional problem that the sample is usually collected in private, raising security and handling issues, such as sample tampering.

Therefore, it is preferable in some situations to conduct analysis on a saliva sample rather than on a urine sample. When applicable, saliva collection and analysis has several advantages over urine collection analysis. A saliva specimen can be taken at any convenient time, and can be obtained singly or sequentially. Moreover, saliva sampling may be done at any location and can be easily observed, if required.

Devices for collecting and analyzing saliva samples have been developed and introduced commercially. Such devices are generally divided into two types. The first type adopts a configuration wherein a collecting part is separated from the analyzing part. The second type adopts a configuration similar to a mid-stream urine pregnancy test, where samples are collected on a pad and delivered by capillary action to the testing channel in the same device.

However, the first type of devices requires multiple steps and may raise the issue of sample contamination. The second type of devices, which is a major improvement over the first type, is able to perform the sample collection and assay in one step. However, since the second type of devices has to serve both purposes of sample collecting and sample delivering, it requires a soft pad for collecting the sample and a rigid pad for delivering the sample to the testing channel. Further, since the pads cannot be squeezed, it needs a large liquid capacity with minimum retention volume. All these requirements render the designing and selection of padding materials difficult. In addition, since the testing device is attached to the collection pad, it is relatively inconvenient to handle the testing device and very likely to have fluids spilled over the whole device.

Accordingly, it is desirable and advantageous to develop a novel device, which have a separate section to implement sample collection independently and still maintains the functionality of one-step sample assay.

SUMMARY OF THE INVENTION

The present invention provides a device for collecting and analyzing a biological fluid. The device contains a sample collecting section having at least one collection pad for collecting a sample of the biological fluid, a sample accommodating section operatively engageable with the sample collecting section for extracting and accommodating the sampled collected by the sample collecting section, and a sample analyzing section, disposed within the sample accommodating section and having a sample analyzing means in fluid communication with the sample extracted and accommodated within the sample accommodating section.

In one aspect of the device, the sample collecting section contains a knob at the proximal end thereof for an operator to hold the sample collection section and an elongate shaft at the distal end therefore for attaching the collection pad. Preferably, the sample accommodating section contains a sample extracting means disposed within the sample accommodating section for engaging the collection pad and extracting the sample collected by the collection pad when the sample collecting section is operatively engaged with the sample accommodating section. Preferably, the sample extracting means contains a protrusion provided within the sample accommodating section and dimensioned to partly engage the collection pad to extract the sample from the collection pad when the sample collecting section is operatively engaged with the sample accommodating section. Preferably, the sample accommodating section has a lower inner surface, and the protrusion is formed on part of the lower inner surface to form a sample reservoir around the protrusion where the sample extracted by the protrusion is accommodated. Preferably, the sample analyzing means of the sample analyzing section is in fluid communication with the sample accommodated in the sample reservoir.

In another aspect of device, the sample collecting section contains an externally threaded portion and the sample accommodating portion contains an internally threaded portion engageable with the externally threaded portion.

In another aspect of the device, the device further contains an insulating means for securing the tight contact between the sample collecting section and the sample accommodating section when the sample collecting section and the sample accommodating section are engaged with each other.

In another aspect of the device, the analyzing means of the sample analyzing section contains a plurality of testing strips. Preferably, the sample analyzing section contains a sleeve with a plurality of grooves formed therein and each of the testing strips is slidably disposed within a corresponding groove.

In another aspect of the device, the sample accommodating section contains a transparent part for viewing the analyzing means of the sample analyzing section.

Although the device according to an exemplary embodiment of the invention will be described in connection with the collection and analysis of oral biological fluid such as saliva, it should be recognized that the application of the device is not limited to oral biological fluids. Rather, the device is applicable to any other suitable circumstances, where collection and analysis of any suitable biological fluids is required.

BRIEF DESCRIPTION OF THE DRAWINGS

These and other features, benefits and advantages of the present invention will become apparent by reference to the following text figures, with like reference numbers referring to like structures across the views, wherein.

DETAILED DESCRIPTION OF THE INVENTION

The present invention now will be described in detail hereinafter with reference to the accompanying drawings, in which preferred embodiments of the invention are shown. However, this invention may be embodied in many different forms and should not be construed as limited to the embodiments set forth herein. Like numerals refer to like elements throughout.

Figure 1:
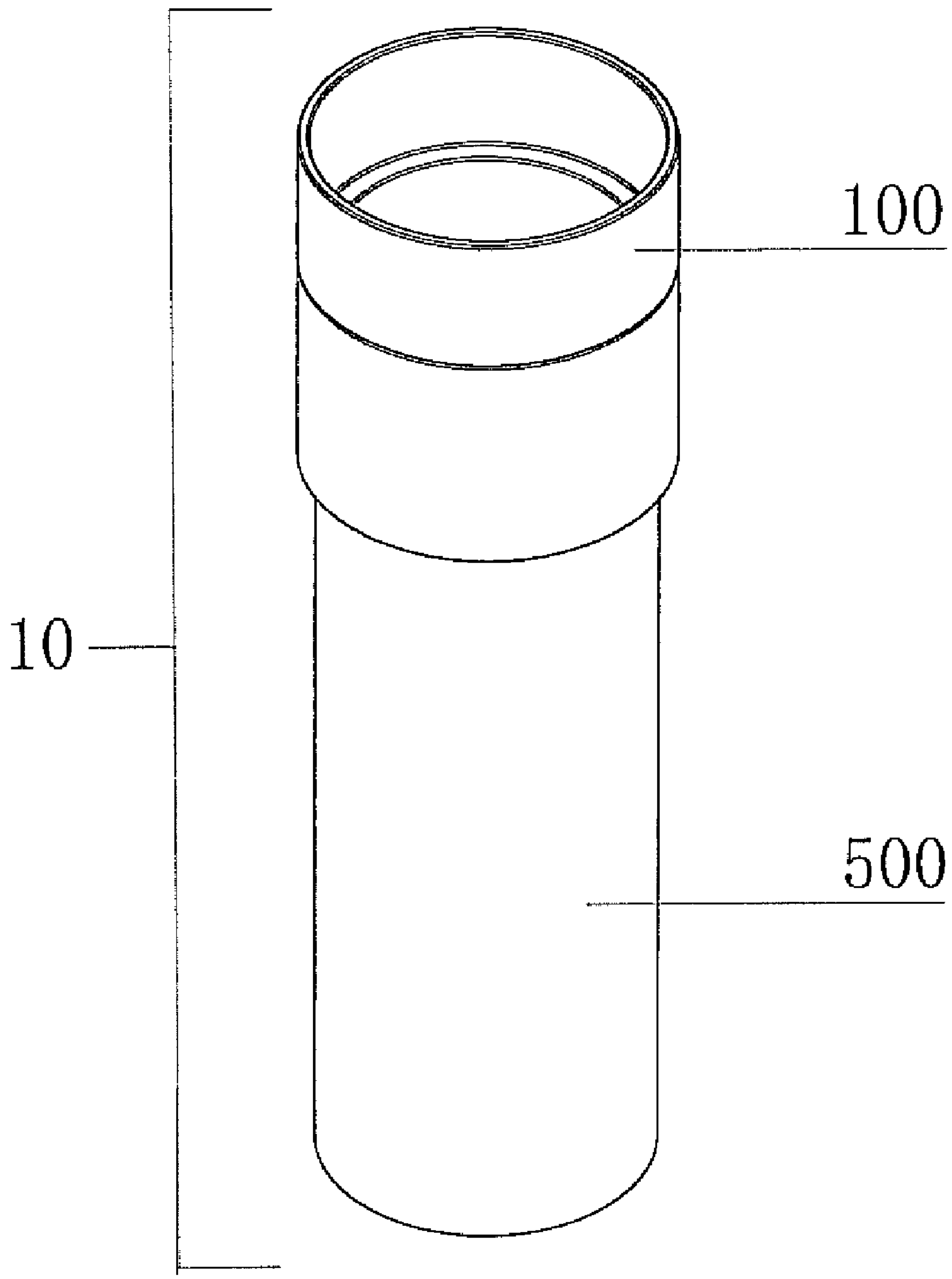
FIG. 1 is an overall perspective view of a device in an assembled state according to an exemplary embodiment of the present invention.
Figure 2:
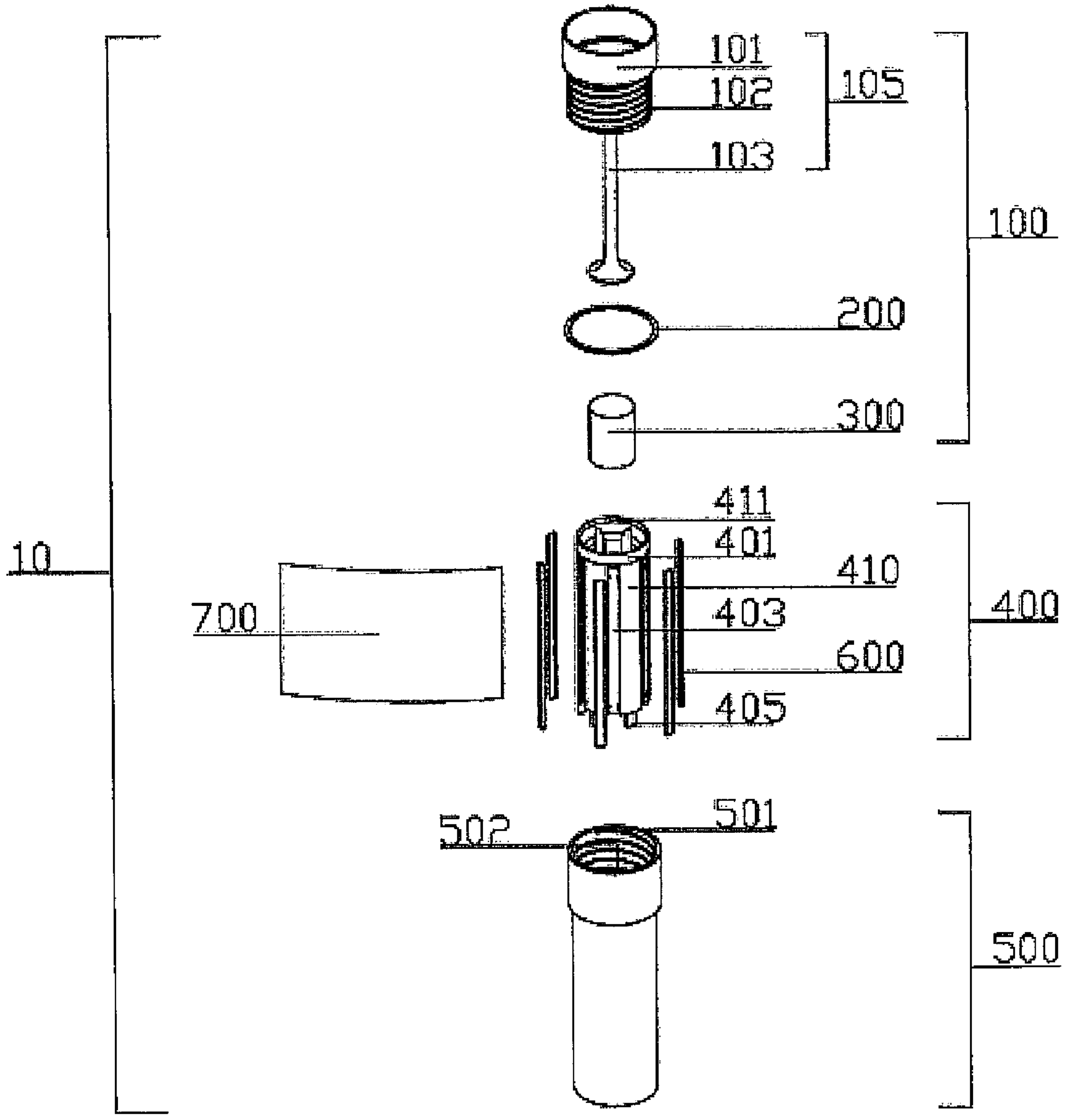
FIG. 2 is an exploded perspective view of the device in an disassembled state according to an exemplary embodiment of the present invention, illustrating different sections of the device in a disassembled state.

FIG. 1 and FIG. 2 illustrate the components of a sample collection and analysis device according to one exemplary embodiment of the invention in an assembled state and a disassembled state, respectively. As shown in the figures, the sample collection and analysis device 10 basically includes a sample collecting section 100, a sample analyzing section 400 and a sample accommodating section 500. The sample collecting section 100 collects samples of biological fluids, such as saliva or blood, from a sample donor. In this exemplary embodiment, the sample collecting section 100 is inserted into and engaged with the sample accommodating section 500 by any suitable means and measures. The sample accommodating section 500 functions to extract and accommodate the sample collected by the sample collecting section 100. The sample analyzing section 400 is disposed within the sample accommodating section 500 and provided with a sample analyzing means in fluid communication with the sample extracted and accommodated by sample accommodating section 500. The sample analyzing means reacts with the collected sample within the sample accommodating section and shows the analysis results by means of, for example, color changing of the analyzing means. A detailed description of the components of the device and connection of the components will be made with reference to the figures.

Figure 3B:
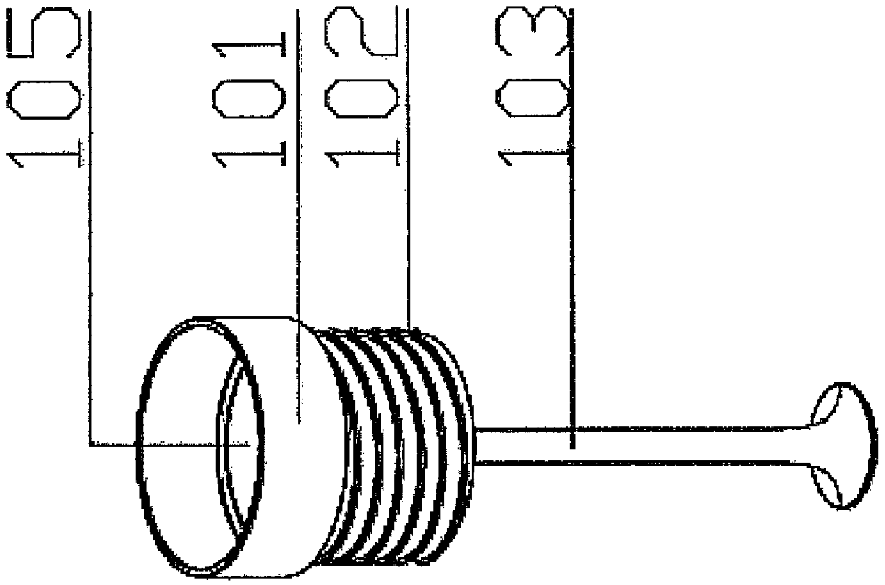
FIGS. 3A and 3B are perspective views of the sample collecting section of the device according to an exemplary embodiment of the present invention.
Figure 3A:
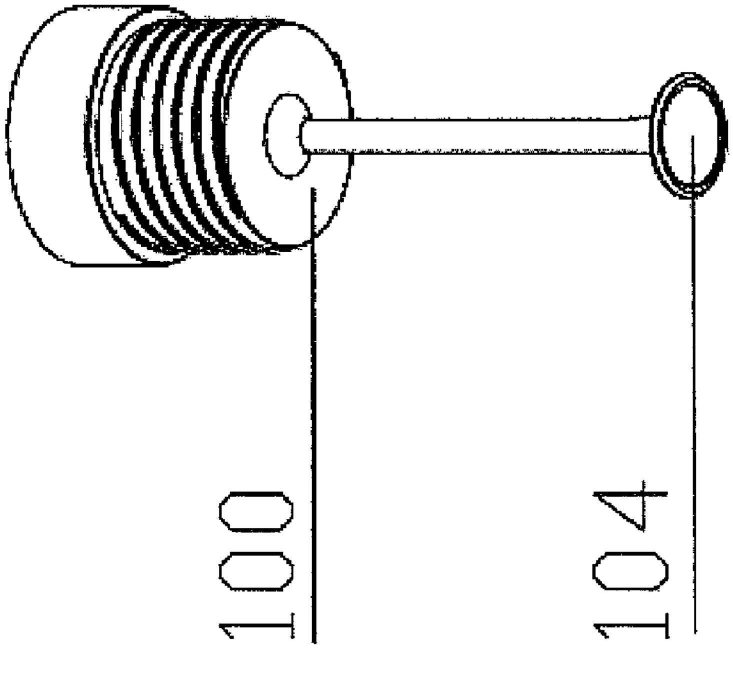

As illustrated in FIG. 1 and FIGS. 3A and 3B, the sample collection section 100 contains a lid 105, including a knob 101 disposed at the proximal end of the lid, an externally threaded portion 102 and an elongated shaft 103 disposed at the distal end of the lid. The lid including the knob, the externally threaded portion and the shaft can be formed integrally or separately, depending on the application circumstances of the device. For example, the lid 105 is a single piece plastic-molded element, for reducing manufacturing costs and saving assembling steps. The knob 101 is disposed at the proximal end of the lid to provide a structure for an operator, such as an examiner or a sample donor, to hold and rotate the lid relative to the sample accommodating section 500. The externally threaded portion 102 is engageable with an internally threaded portion 502 of the sample accommodating section 500, which will be described in detail later. However, it should be recognized that the engagement between the sample collecting section 100 and the sample accommodating section 500 could be implemented by any suitable engaging means and measures, other than the threaded engagement, such as snap fit, flexible protrusion and indent, and so on.

The elongated shaft 103 provides a structure for attaching a sample collection pad 300, which is normally made of sponge material. As shown in FIGS. 3A and 3B, the elongated shaft 103 can further comprises a flattened tip 104 to provide an enlarged attaching area to secure the attachment of the collection pad. The collection pad 300 can be attached to the shaft by any suitable means and measure, such as gluing. The elongated shaft 103 should have a sufficient longitudinal dimension extending from the externally threaded portion 102 of the lid, for an operator to collect samples, such as saliva from a sample donor's mouth. When there is a need to collect an oral sample from a donor, the operator rotates the knob 101 of the sample collecting section 100, separates the sample collecting section from the sample accommodating section 500, and hands over the sample collection section 100, including the lid 105 and the collection pad 300 attached to the lid, to the donor. Subsequently, the donor holds the knob 101 and inserts the shaft 103 into his/her mouth. The donor needs to rotated the lid and rub his/her mouth for a certain time, for example, 1 to 5 minutes, until the collection pad 300 is saturated with oral fluid.

Referring to FIGS. 1, 5A, 5B and 6, the sample accommodating section 500 will be described in detail with reference to these figures. The sample accommodating section 500 can assume any suitable shape. In this exemplary embodiment, the sample accommodating section 500 generally takes the shape of a cylinder. The sample accommodating section 500 includes an internally threaded portion 502, which engages the externally threaded portion 102 of the lid 105. Accordingly, the coupling of lid 105 and the sample accommodating section 500 can be tightened by rotating the lid relative to the sample accommodating section 500. In order to further strengthen the engagement between the lid and the sample accommodating section and prevent the leakage of collected sample, an insulating element, for example a rubber O-ring 200, can be provided between the lower rim of knob 101 and the upper rim of internally threaded portion 502 of the sample accommodating section 500.

Figure 6:
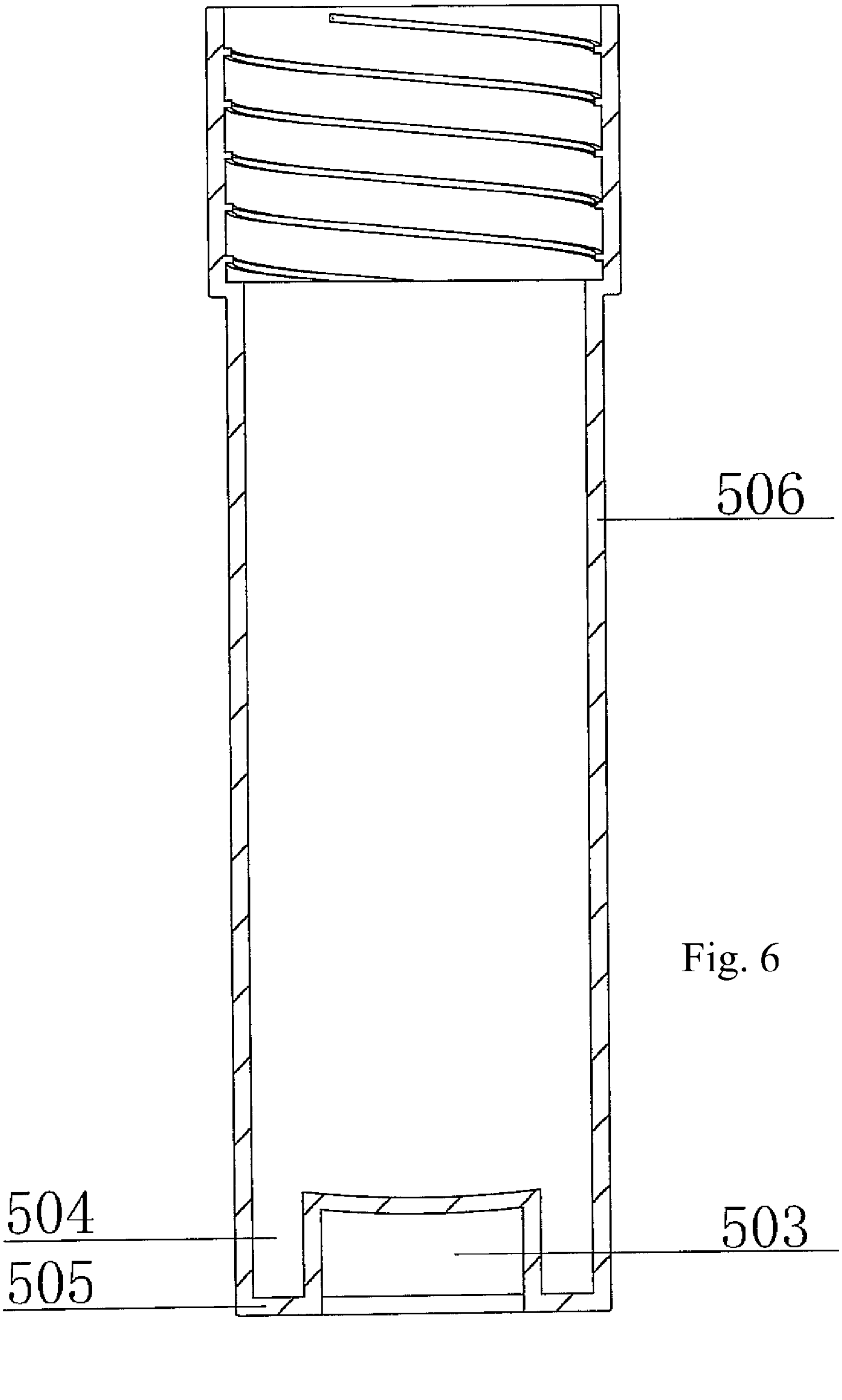
FIG. 6 is a sectional view of the sample accommodating section of the device according to an exemplary embodiment of the present invention.

Referring to FIG. 6, the sample accommodating section 500 further contains a protrusion 503 formed within the sample accommodating section 500, for partially engaging the collection pad 300 to extract or squeeze the collected sample out of the collection pad 300 when the sample collecting section 100 is rotated into the sample accommodating section 500. The protrusion 503 can assume any suitable shapes, dimensions and locations, as long as it is capable of at least partially engaging with the sample collection pad. In this exemplary embodiment, the protrusion 503 is formed on a lower inner surface 505 and extending from the lower inner surface upwardly. The dimensions, including horizontal and vertical dimensions, of the protrusion 503 can be adapted to control the amount or percentage of the collected sample extracted from the collection pad 300. For example, the dimensions of the protrusion 503 can be adapted such that about 70% of the collected sample is extracted from the collection pad 300 when the sample collecting section 100 is fully rotated into the sample accommodating section 500. The remaining sample contained within collection pad 300 can be reserved for later analysis.

As illustrated in FIG. 6, a sample reservoir 504 is formed by the inner lower surface 505, the protrusion 503 and an outer surface 506 of the sample accommodating section 500. The shape and capacity of the sample reservoir 504 can be adjusted by altercating the shapes and dimensions of the protrusion 503, the inner lower surface 505 and the outer surface 506.

Figure 4A:
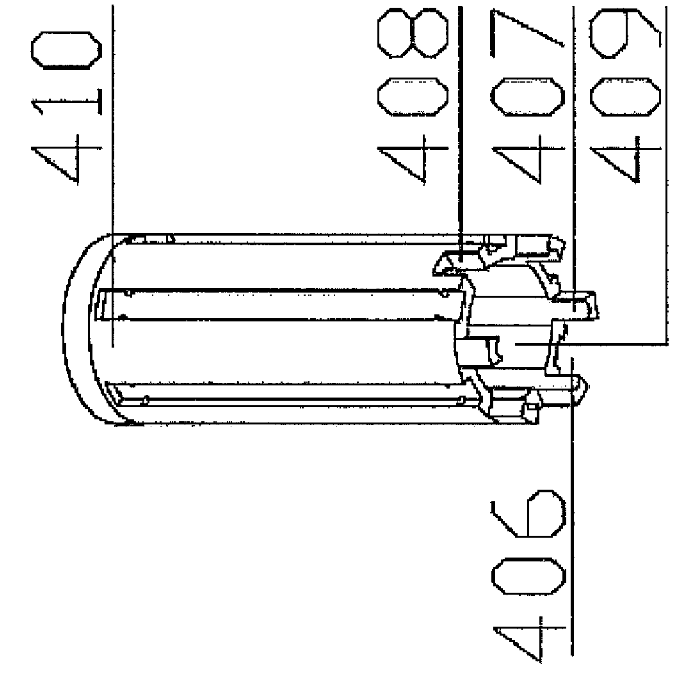
FIG. 4A is an perspective view of the sample analyzing section of the device according to an exemplary embodiment of the present invention and FIG. 4B is an exploded perspective view of the sample analyzing section of the device according to an exemplary embodiment of the present invention.
Figure 4B:
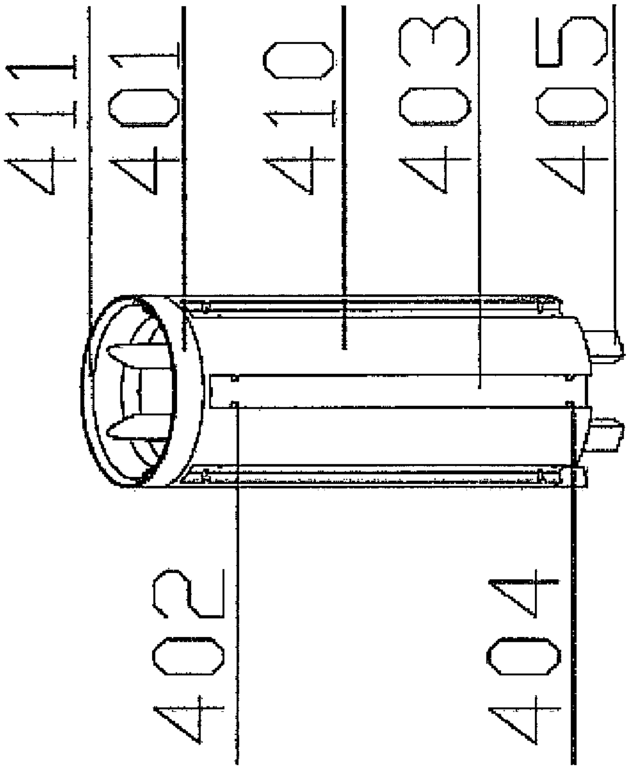
Figure 5B:
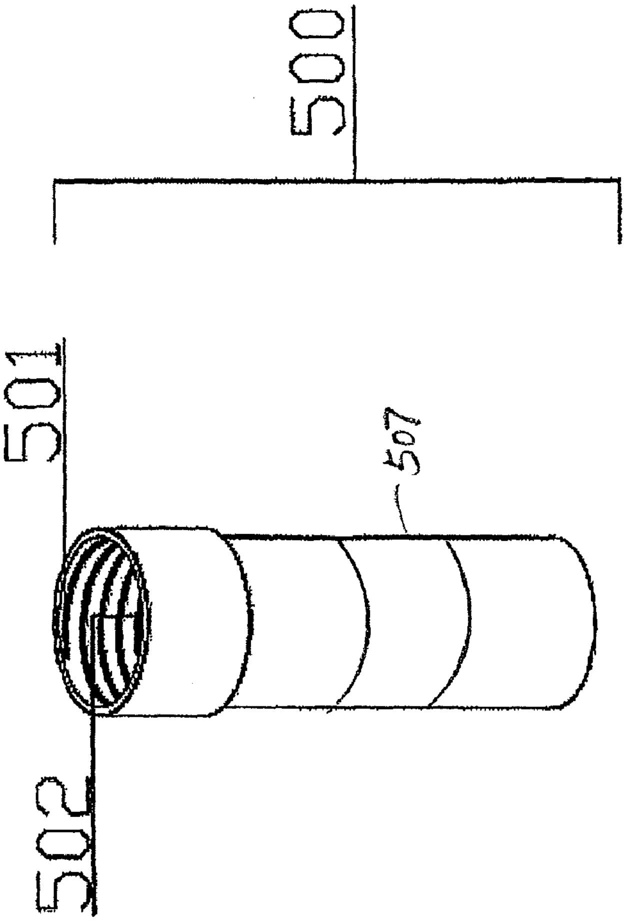
FIGS. 5A and 5B are perspective views of the sample accommodating section of the device according to an exemplary embodiment of the present invention.
Figure 5A:
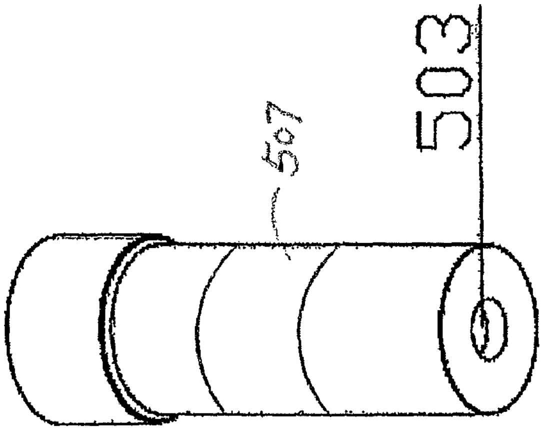

When the collection sample is squeezed out of collection pad 300 after protrusion 503 engages collection pad 300, the extracted sample flows into sample reservoir 504 due to the gravity of the sample. The reservoir provides a structure rendering fluid communication of the sample and the sample analyzing means of the sample analyzing section 400, which will be described below with reference to FIGS. 1, 4A and 4B.

In this exemplary embodiment of the device, sample analyzing section 400 is generally a hollow sleeve disposed within the sample accommodating section and through which shaft 103 and collection pad 300 pass. However, it should be recognized that the sample analyzing section could take any suitable shape and configuration to fulfill the functionality of sample analysis.

As illustrated in FIG. 2, the sample analyzing section 400 contains an approximately round sleeve 410, a rim 411 disposed at the upper end of the sleeve 410, a plurality of lower end extensions 405 formed at the lower end of the sleeve 410 and a plurality of grooves 403 formed along the outer surface of sleeve 410 and extending downwardly to the lower end of sleeve 410. The sample analyzing section 400 further contains a plurality of analyzing means, for example, a plurality of analyzing stripes 600 slidably disposed within the grooves 403. Practically, the dimension of the sleeve 410 is larger than the dimension of the protrusion 503, and the lower end extensions 405 are higher than the protrusion 503, such that the sleeve 410 sits on the inner lower surface 50 of the sample accommodating section 500 with the lower end extensions 405 spread around the protrusion 503 in the sample reservoir 504. Significantly, the strips 600 extend beyond the lower end of sleeve 410 and further extends into the sample reservoir 504. Thus, the strips 600 are in fluid communication with the sample contained in the sample reservoir 504 when the sample collecting section 100 is inserted into the sample accommodating section 500 and the sample collected by the collection pad 300 is squeezed out by the protrusion 503. Although FIG. 2 shows five analyzing strips, the number and type of the analyzing strips can vary depending on the application circumstances of the device.

Normally, when the sample is extracted from the collection pad 300 after the engagement of the collection pad 300 and the protrusion 503 and subsequently accumulated in the sample reservoir 504, the sample is absorbed by the analyzing strips 600, and consequently a series of immunoassays are performed. The assay usually can be accomplished within 10 minutes and the test results can be demonstrated by means of any physical or chemical changes of the trip that are perceptible or detectable by the operator.

For example, the sample accommodating section 500 may further includes a transparent portion 507, which provides a structure for viewing the testing results directly. In addition, an optional label 700 can be provided to cover the transparent portion 507 before the assay of the sample and removed from the transparent portion 507 to render an observing window after the assay of the sample. The label 700 can be utilized to provide information concerning the properties of the assay to be performed. For example, five DOA test strips are used for common drugs of abuse screen when conducting an on-site examination. When the fluid sample is negative for drugs abuse, each strip will generate a colored test line and a colored control line. In the event any of the testing drugs is presented in the sample fluid, the test line will be colorless on a specified analyzing strip. By reading the results through the transparent window of the sample accommodating section, a quick and accurate determination can be made on whether the sample donor has taken drugs and the type of the drugs.

In case that a quantitative test or a confirmation test is required, the on-site operator needs to send the remaining sample to a qualified lab for further analysis. The above exemplary embodiment of the invention is able satisfy the foregoing requirement. First, the sample absorbed by the analyzing strips does not backflow to reach the remaining sample collected in the collection pad and thus prevent the potential contamination of the remaining sample. Further, the device provides a leak-proof container for the sample fluid during the transportation of the sample. Thus, the change for the sample to spill over is minimized. In addition, since the only portion of the device that is touched by an operator is the lid, the chance for the operation to touch and smell the sample is also minimized, which improves the safety of the operator.

In an experiment, sample collection and analysis were performed on five volunteers, each of who rubbed his/her mouth with a collection pad for 5 minutes and then inserted the pad into the cylinder to initiate a sample assay by squeezing the collection pad. The immunoassay was completed within 10 minutes and the results were observed through the transparent window. The following Table 1 records the results. As a positive saliva control, an artificial saliva control containing a specified drug mixture at a concentration of two times of a specified cutoff value was used for demonstration, and five repetitive tests were performed by soaking a collection pad into the saliva control.

TABLE 1

| Sample | Morphine | Cocaine | THC | Amphetamine | Methamphetamine |
|---|---|---|---|---|---|
| Negative* (5) | – | – | – | – | – |
| Positive** (5) | + | + | + | + | + |

*A negative drug test result will have a purple color at the test line. When read against a colored chart, the color intensity shall be over score 3.
**A positive drug test result will have no color at the test line. When read against a colored chart, the color intensity shall be below score 3.

The invention has been described herein with reference to particular exemplary embodiments. Certain alterations and modifications may be apparent to those skilled in the art, without departing from the scope of the invention. The exemplary embodiments are meant to be illustrative, not limiting of the scope of the invention, which is defined by the appended claims.

What is claimed is:

1. A device for collecting and analyzing a biological fluid, comprising:

a sample collecting section comprising at least one collection pad for collecting a sample of the biological fluid and a first threaded portion;

a unitary sample accommodating section for extracting and accommodating the sample collected by the sample collecting section, the sample accommodating section comprising a second threaded portion operatively engageable with the first threaded portion of the sample collecting section, the sample accommodating section further comprising a sample extracting means disposed within the unitary sample accommodating section, the sample extracting means being configured to engage the at least one collection pad for extracting the sample from the collection pad in a controlled manner when the first threaded portion and the second threaded portion engage each other, the unitary sample accommodating section being a sole chamber therein;

a sample reservoir provided circumferentially along the sole chamber and within the sole chamber; and a sample analyzing section at least partially arranged within the reservoir, the sample analyzing section comprising: a tubular sleeve having a passageway through which the at least one collection pad passes to engage the sample extracting means; a plurality of grooves formed along an outer surface of the sleeve; and a plurality of testing strips each slidably disposed within a corresponding groove to be in fluid communication with the sample extracted and accommodated within the unitary sample accommodating section.

2. The device of claim 1, wherein the sample collecting section comprises a knob at the proximal end thereof for an operator to hold the sample collection section and an elongate shaft at the distal end thereof for attaching the collection pad.

3. The device of claim 1, wherein the sample extracting means comprises a protrusion provided within the unitary sample accommodating section and dimensioned to at least partly engage the collection pad to extract the sample from the collection pad when the first threaded portion and the second threaded portion engage each other.

4. The device of claim 3, wherein the unitary sample accommodating section has a lower inner surface on which the protrusion is formed, and the reservoir is formed around the protrusion in the sample accommodating section.

5. The device of claim 4, wherein the testing strips of the sample analyzing section are in fluid communication with the sample accommodated in the sample reservoir.

6. The device of claim 1, wherein the first threaded portion comprises an externally threaded portion and the second threaded portion comprises a complementary internally threaded portion.

7. The device of claim 1, further comprising an insulating means for securing the tight contact between the sample collecting section and the unitary sample accommodating section when the sample collecting section and the unitary sample accommodating section are engaged with each other.

8. The device of claim 1, wherein the unitary sample accommodating section comprises a transparent part for observing the analyzing means of the sample analyzing section.

9. The device of claim 1, wherein the engagement between the at least one collection pad and the sample extracting means can be controlled by the engagement between the first threaded portion and the second threaded portion such that the amount of sample extracted from the collection pad can be controlled.

* * * * *